United States Patent
Mallin et al.

(10) Patent No.: US 10,441,338 B2
(45) Date of Patent: Oct. 15, 2019

(54) BALLOON CATHETER WITH FLUID INJECTION ELEMENTS

(71) Applicant: MEDTRONIC CRYOCATH LP, Toronto (CA)

(72) Inventors: George D. Mallin, Quebec (CA); Claudia Lueckge, Quebec (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 750 days.

(21) Appl. No.: 14/154,747

(22) Filed: Jan. 14, 2014

(65) Prior Publication Data

US 2015/0196740 A1 Jul. 16, 2015

(51) Int. Cl.
*A61B 18/02* (2006.01)
*A61B 18/00* (2006.01)

(52) U.S. Cl.
CPC ...... *A61B 18/02* (2013.01); *A61B 2018/0022* (2013.01); *A61B 2018/00255* (2013.01);
(Continued)

(58) Field of Classification Search
CPC ............ A61B 5/6853; A61B 17/12136; A61B 2017/22054; A61B 2017/22055;
(Continued)

(56) References Cited

U.S. PATENT DOCUMENTS 6,106,518 A * 8/2000 Wittenberger ......... A61B 18/02
606/21
6,575,933 B1 * 6/2003 Wittenberger ......... A61B 18/02
128/898
(Continued)

FOREIGN PATENT DOCUMENTS

CN 103118613 A 5/2013
EP 1303226 A2 4/2003
(Continued)

OTHER PUBLICATIONS

Xue Zhao et al., Pulmonary Antrum Radial-Linear Ablation for Paroxysmal Atrial Fibrillation: Interim Analysis of a Multicenter Trial, Circulation Arrhythimia and Electrophysiology Journal of the American Heart Association, Downloaded from circep.ahajournals. org by guest on Apr. 22, 2013, pp. 310-321.
(Continued)

*Primary Examiner* — Ronald Hupzey, Jr.
(74) *Attorney, Agent, or Firm* — Christopher & Weisberg, P.A.

(57) ABSTRACT

A system and method for creating radial-linear lesions in tissue. The system includes a cryoablation device having a first balloon, a second balloon disposed about the first balloon, and one or more splines disposed between the first balloon and second balloon, each spline defining a plurality of ports. The splines may be in communication with a coolant supply, and the first balloon may be in communication with a coolant supply or non-coolant inflation fluid supply. When the first balloon is in the uninflated configuration, the splines may have a substantially linear configuration. Each of the splines may be radially oriented about an elongate shaft and transitionable between the substantially linear configuration and an arcuate configuration when the first balloon is in the inflated configuration. Coolant expelled from the splines between the first and second balloons creates an ablation pattern on the outer surface of the second balloon.

20 Claims, 10 Drawing Sheets

(52) U.S. Cl.
CPC .............. *A61B 2018/00267* (2013.01); *A61B 2018/00351* (2013.01); *A61B 2018/00357* (2013.01); *A61B 2018/00375* (2013.01); *A61B 2018/0212* (2013.01); *A61B 2018/0262* (2013.01)

(58) Field of Classification Search
CPC ........... A61B 2017/320048; A61B 2018/0022; A61B 2018/00255; A61M 25/1001; A61M 2025/1011; A61M 2025/1013; A61M 2025/1084
See application file for complete search history.

(56) References Cited

U.S. PATENT DOCUMENTS

| | | | | |
|---|---|---|---|---|
| 6,602,247 | B2* | 8/2003 | Lalonde | A61M 25/0029 606/21 |
| 7,794,455 | B2* | 9/2010 | Abboud | A61B 18/02 606/21 |
| 8,012,147 | B2* | 9/2011 | Lafontaine | A61B 18/02 606/20 |
| 8,945,107 | B2* | 2/2015 | Buckley | A61B 18/02 606/21 |
| 2002/0062122 | A1* | 5/2002 | Lehmann | A61B 18/02 606/23 |
| 2003/0088240 | A1* | 5/2003 | Saadat | A61B 18/02 606/21 |
| 2008/0312644 | A1* | 12/2008 | Fourkas | A61B 18/02 606/22 |
| 2009/0234345 | A1* | 9/2009 | Hon | A61B 18/02 606/21 |
| 2009/0299355 | A1 | 12/2009 | Bencini et al. | |
| 2010/0241112 | A1 | 9/2010 | Watson | |
| 2013/0197497 | A1 | 8/2013 | Wittenberger et al. | |
| 2013/0197499 | A1* | 8/2013 | Lalonde | A61B 18/02 606/21 |
| 2013/0345688 | A1* | 12/2013 | Babkin | A61B 18/02 606/20 |
| 2014/0316398 | A1* | 10/2014 | Kelly | A61B 18/02 606/24 |

FOREIGN PATENT DOCUMENTS

| | | |
|---|---|---|
| EP | 1424950 A2 | 6/2004 |
| WO | 200207625 A2 | 1/2002 |
| WO | 2003020334 A2 | 3/2003 |
| WO | 2013019385 A1 | 2/2013 |

OTHER PUBLICATIONS

Hugh Calkins, Has the Time Come to Abandon the Concept That "Pulmonary Vein Isolation Is the Cornerstone of Atrial Fibrillation Ablation"?, Circulation Arrhythmia and Electrophysiolog Journal of The American Heart Association, Downloaded from circep.ahajournals.org at Medtronic, Inc.—on Apr. 22, 2013, pp. 241-243.

International Search Report and Written Opinion dated Feb. 24, 2015, for corresponding International Application No. PCT/CA2014/000885; International Filing Date: Dec. 15, 2014 consisting of 7-pages.

Notice on the First Office Action for Application No. 201480073045.X, Applicant: Medtronic CryoCath LP, Title: Balloon Catheter With Fluid Injection Elements, dated Apr. 19, 2017, including English Translation, 18 pages.

* cited by examiner

BALLOON CATHETER WITH FLUID INJECTION ELEMENTS

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for creating linear lesions in a target tissue. Specifically, the invention relates to a cryoablation method and system for creating radial-linear lesions to treat atrial fibrillation originating from within or proximate a pulmonary vein.

BACKGROUND OF THE INVENTION

Minimally invasive surgical techniques are known for performing medical procedures within the cardiovascular system, and a number of medical conditions may be treated using ablative techniques and devices. For example, cryoablation, or the removal of heat from body tissue to "stun" or kill the tissue cells, is one technique that has proven effective in the treatment of many kinds of cardiac arrhythmias.

One such arrhythmia, atrial fibrillation, is a medical condition resulting from abnormal electrical activity within the heart. This abnormal activity may occur at regions of the heart including the sino-atrial (SA) node, the atrioventricular (AV) node, the bundle of His, or within other areas of cardiac tissue. Moreover, atrial fibrillation may be caused by abnormal activity within an isolated focal center within the heart. These foci can originate within a pulmonary vein, and particularly the superior pulmonary veins. Atrial fibrillation may be treatable by ablation of the abnormal tissue within the left atrium and/or the pulmonary vein. In particular, minimally invasive techniques, such as those described above, use ablation catheters to target the pulmonary vein in order to ablate any identified foci having abnormal electrical activity.

A procedure called pulmonary vein isolation (PVI) is commonly used to treat atrial fibrillation. This procedure involves the use of a cryogenic device, which is generally positioned at the ostium of a pulmonary vein (PV) such that any blood flow exiting the PV into the left atrium (LA) is completely blocked. At this position the cooling of the balloon system may be activated for a sufficient duration to create a desired lesion at the PV-LA junction. If a cryoballoon is used as the treatment element of the cryogenic device, the balloon is typically inflated using a fluid coolant, enabling the balloon to create a lesion about the ostium and/or antrum of the PV to disrupt aberrant electrical signals exiting the PV. However, although this method may be effective in treating atrial fibrillation in the short term, recent studies indicate that long-term success ranges from about 70% to about 80%.

A newer method of treating atrial fibrillation is called PV antrum radial-linear (PAR) ablation, and research indicates that this method may be more effective than PVI. Instead of creating a circumferential lesion about the PV ostium and/or antrum as in PVI, the PAR ablation technique involves the creation of one or more linear lesions in different radial directions from one or more PV ostia into the PV/left atrium (LA) junction. To create linear lesions of a sufficient depth to disrupt the aberrant electrical signals, however, the treatment element of an ablation device such as a focal catheter may have to be repeatedly traced over the linear lesions. This can be a time-consuming process and user error may lead to non-linear lesions and ablation of non-target tissue.

In view of the above, it is desirable to provide for an ablation device that can be used to quickly and easily perform a PAR ablation procedure in the treatment of, for example, atrial fibrillation.

SUMMARY OF THE INVENTION

The present invention advantageously provides a device, system, and method for creating radial-linear lesions in tissue. In one embodiment, the device may generally include a first balloon, a second balloon disposed about the first balloon, and one or more splines disposed between the first balloon and second balloon, each spline defining a plurality of ports. The one or more splines may be in fluid communication with a first fluid supply, and the first balloon may be in fluid communication with at least one of the first fluid supply and a second fluid supply. Additionally the first balloon may be transitionable between an uninflated configuration and an inflated configuration. The first fluid supply may be a coolant, whereas the second fluid supply may be a coolant or a non-coolant inflation fluid. The device may further include an elongate body and an elongate shaft disposed within and extending distally from the elongate body. When the first balloon is in the uninflated configuration, the one or more splines may have a substantially linear configuration, and may be substantially parallel to the longitudinal axis of the shaft. Further, each of the one or more splines may be radially oriented about the elongate shaft and transitionable between the substantially linear configuration and an arcuate configuration. Each spline may have a distal portion and a proximal portion, with both the distal portion and proximal portion being located within the first balloon. The plurality of ports may be located on (or defined by) the distal portion of each spline, the proximal portion of each spline, or along the length of the portion of spline located within the first balloon.

In one embodiment, the system may generally include a cryoablation device defining a longitudinal axis and including an elongate body having a distal portion and a proximal portion, an elongate shaft disposed within the elongate body, the elongate shaft having a distal portion and a proximal portion, a first balloon coupled to the distal portion of the elongate shaft, a second balloon disposed about the first balloon and being coupled to the distal portion of the elongate shaft and the and the distal portion of the elongate body, and one or more splines disposed between the first balloon and second balloon, each spline defining a plurality of ports. The system may further include a control unit being in communication with the cryoablation device and having a first fluid supply in fluid communication with the one or more splines. The system may further include a second fluid supply in communication with the first balloon. The first fluid supply may be a coolant and the second fluid supply may be either a coolant or a non-coolant inflation fluid. The first fluid supply may also be in fluid communication with the first balloon. The first and second balloons may define an interstitial space therebetween, and fluid traveling from the first fluid supply may exit the plurality of ports into the interstitial space.

In one embodiment, the method may generally include positioning a cryoablation device in contact with pulmonary vein antrum tissue of a patient's heart, the cryoablation device having an elongate body having a distal portion, an elongate shaft disposed within the elongate body, one or more conduits within the elongate body and the elongate shaft, and a treatment element having an inner balloon coupled to the elongate shaft and being in fluid communication with the one or more fluid conduits within the elongate shaft, an outer balloon disposed about the inner balloon and being coupled to the elongate shaft and the elongate body and being in fluid communication with the one or more fluid conduits within the elongate body, and one or more longitudinal splines radially disposed between the inner balloon and the outer balloon, each spline defining a plurality of ports, the one or more splines being in fluid communication with a coolant source. The method may further include opening the one or more fluid conduits within the elongate body to the coolant source, coolant from the coolant source passing into the one or more splines and being ejected from the one or more ports into an interstitial space defined between the inner balloon and the outer balloon. The inner balloon may be in fluid communication with a fluid source, and the method may further include positioning the cryoablation device within a left atrium of the patient's heart and opening the one or more fluid conduits within the elongate shaft to the fluid source, fluid from the fluid source passing into and inflating the inner balloon. Further, the one or more splines and the outer balloon may be radially expanded about the inner balloon when the inner balloon is inflated.

BRIEF DESCRIPTION OF THE DRAWINGS

A more complete understanding of the present invention, and the attendant advantages and features thereof, will be more readily understood by reference to the following detailed description when considered in conjunction with the accompanying drawings, which may not be drawn according to scale, wherein.

DETAILED DESCRIPTION OF THE INVENTION

Figure 1:
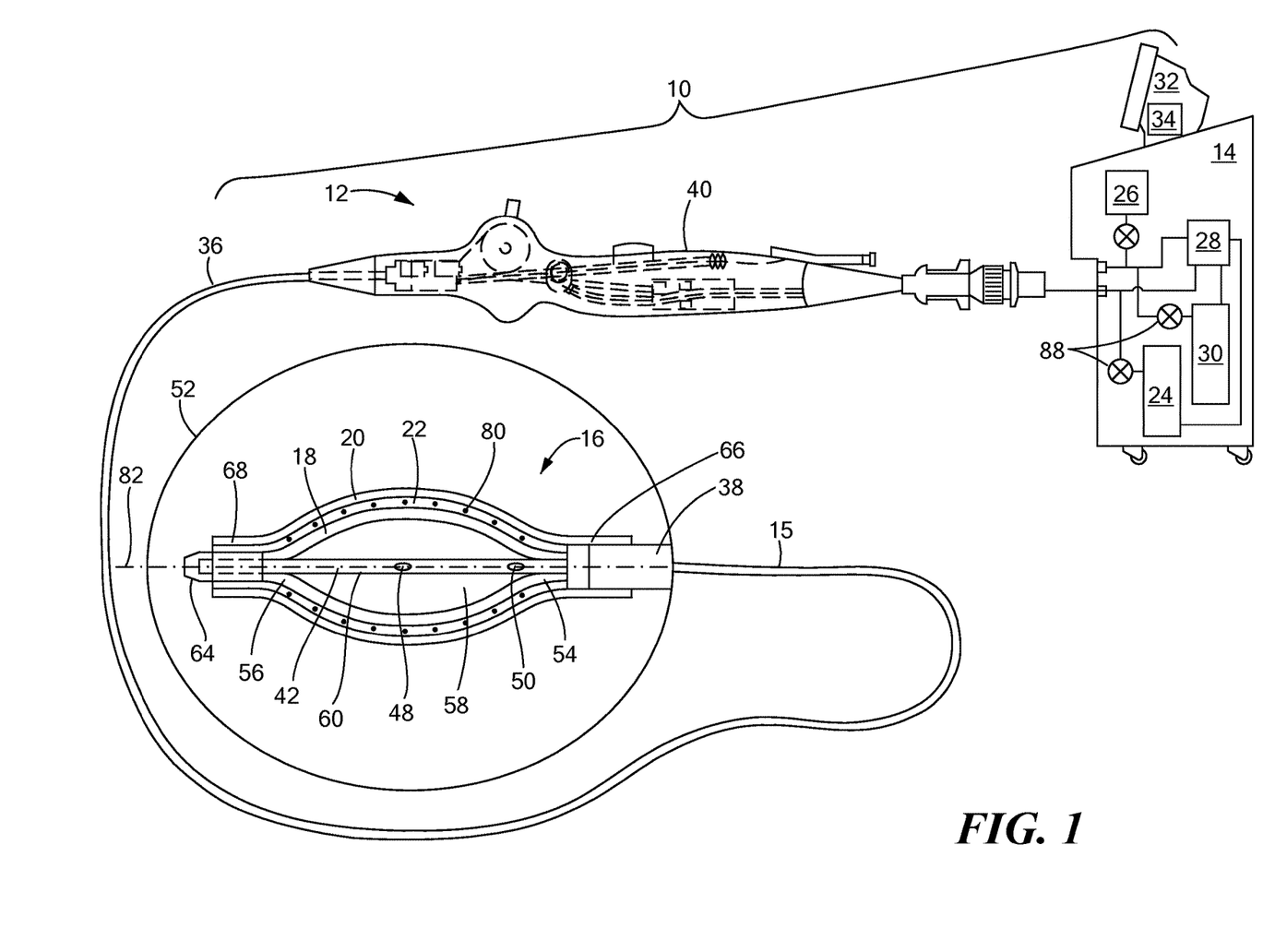
FIG. 1 shows an exemplary medical system including a cryoablation device in accordance with the present invention.

Referring now to the drawing figures in which like reference designations refer to like elements, an embodiment of a medical system constructed in accordance with principles of the present invention is shown in FIG. 1 and generally designated as "10." The system 10 generally includes a medical device 12 that may be coupled to a control unit 14 or operating console. The medical device 12, for example, a cryoablation device as shown in FIG. 1, may generally include an elongate body 15 and one or more diagnostic or treatment elements 16 for energetic, therapeutic and/or investigatory interaction between the medical device 12 and a treatment site. For example, the treatment element 16 may include an inner balloon 18, an outer balloon 20, and one or more splines 22 disposed between the inner 18 and outer balloons 20. The treatment element 16 may deliver, for example, cryogenic therapy to a tissue area in proximity to a treatment region, including cardiac tissue and/or pulmonary vein tissue.

The system 10 may include one or more treatment or diagnostic sources coupled to the device 12 for use in an operative procedure, such as tissue ablation. For example, the control unit 14 may include a fluid supply 24 including one or more reservoirs for one or more coolants, cryogenic refrigerants, or the like, an exhaust or scavenging system for recovering or venting expended fluid for reuse or disposal (including, for example, a recovery reservoir 26 and pump 28), as well as various control mechanisms. The control unit 14 may also include an additional fluid supply 30 including a reservoir containing a non-coolant liquid, gas, or combination liquid and gas used to inflate an inner balloon 18 of the device 12, referred to as "inflation fluid." In addition to providing an exhaust function for the fluid or coolant supply, the control unit 14 may also include pumps 28, valves, controllers or the like to recover and/or re-circulate fluid delivered to various fluid pathways of the medical device 12. A vacuum pump 28 in the control unit 14 may create a low-pressure environment in one or more conduits within the medical device 12 so that fluid is drawn into the conduits/lumens of the elongate body 15, away from the distal portion and toward the proximal portion of the elongate body 15.

The control unit 14 may also include one or more components for the manual and/or automatic regulation of the system, such as a computer 32 having a processor 34 for executing one or more algorithms for the automatic regulation of the device 12 before, during, and after an ablation procedure. For example, the processor 34 may be programmable to inflate and deflate one or more cryoballoons of the treatment element (such as according to a user-programmed duty cycle or an automated duty cycle), to regulate temperature of the treatment element, and/or to receive and interpret mapping or sensor signals from the cryoablation device 12 or another device used as part of a medical procedure. Although various system components may be shown and described herein as being within the control unit 14, the term "control unit" as used herein refers to any system component other than the cryoablation device 12 and other devices that are passed into the patient to perform the medical procedure, regardless of whether the components are physically located within the control unit 14.

Continuing to refer to FIG. 1, the medical device 12 may include an elongate body 15 passable through a patient's vasculature and/or proximate to a tissue region for diagnosis or treatment, such as a catheter, sheath, or intravascular introducer. Accordingly, the elongate body 15 may be composed of a biocompatible material that is sufficiently flexible to safely pass through tortuous pathways of the patient's vasculature. The elongate body 15 may define a proximal portion 36 and a distal portion 38, and may further include one or more lumens or conduits disposed within the elongate body 15 thereby providing mechanical, electrical, and/or fluid communication between the proximal portion of the elongate body 15 and the distal portion of the elongate body 15, as discussed in more detail below. The proximal portion 36 of the elongate body 15 may include a handle 40 having one or more knobs, levers, connectors, umbilicals, and other components used for steering, manipulating, and operating the device 12 and connecting the device 12 to the control unit 14.

The medical device 12 may further include an elongate shaft 42 at least partially disposed within a portion of the elongate body 15. The shaft 42 may extend or otherwise protrude from a distal end of the elongate body 15, and may be movable with respect to the elongate body 15 in longitudinal and rotational directions. That is, the shaft 42 may be slidably and/or rotatably moveable with respect to the elongate body 15. Alternatively, the shaft 42 may be affixed or coupled to the elongate body 15 such that the shaft 42 has a fixed position and is not slidably and/or rotatably moveable with respect to the elongate body 15. Further, the shaft 42 may be as flexible, more flexible, or less flexible than the elongate body 15. For example, if it is desirable to provide a device with a distal portion that is more easily steerable or bendable than the elongate body, then the shaft 42 may be more flexible (that is, be composed of a material having a lower flexural modulus) than the elongate body 15. Conversely, if a more rigid distal portion is desired, the shaft 42 may be less flexible or more rigid (that is, be composed of a material having a higher flexural modulus) than the elongate body 15.

The shaft 42 may include or define an inner balloon fluid delivery lumen or conduit that is in fluid communication with the coolant supply 24 to deliver a fluid from the proximal portion 36 of the elongate body 15 and/or the control unit 14 to the distal portion 38 of the elongate body 15 and/or treatment region 16 of the device 12. Additionally or alternatively, the inner balloon fluid delivery conduit may be in fluid communication with an inflation fluid reservoir 30 containing a non-coolant fluid (liquid, gas, or combination thereof). The shaft 42 may also include or define an inner balloon fluid recovery conduit that is in fluid communication with the scavenging system. Further, the shaft 42 may include one or more fluid ejection ports 48 for expelling fluid into the inner balloon 18 of the treatment element and one or more fluid recovery ports 50 for removing expended coolant and/or inflation fluid from the inner balloon 18.

Figure 3:
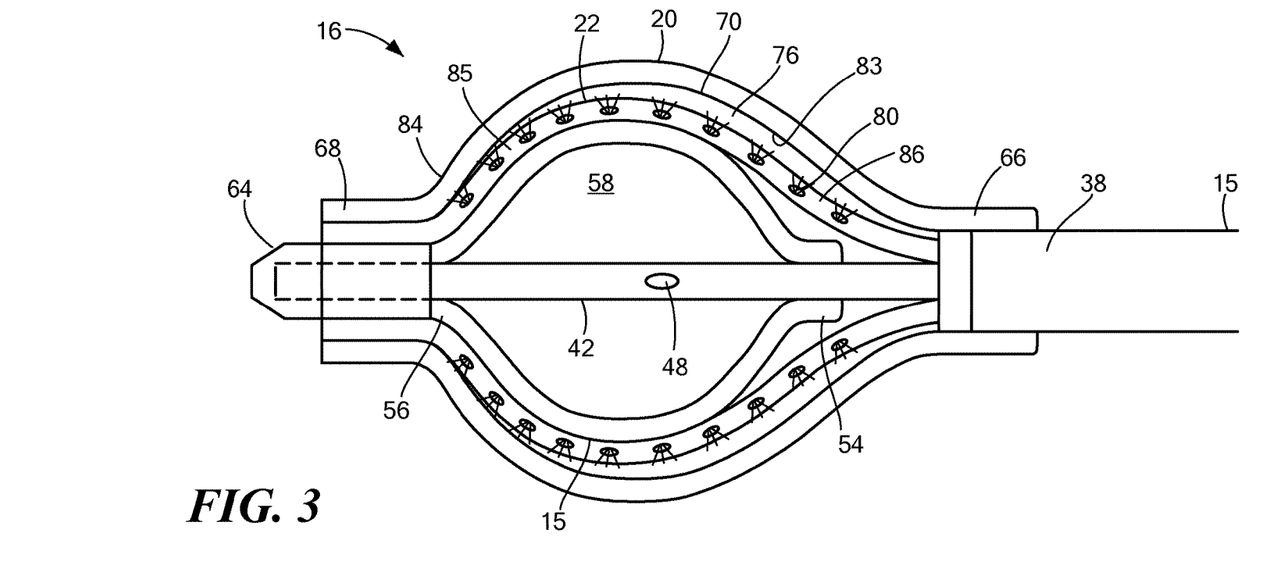
FIG. 3 shows a cross-sectional view of a distal portion of a first exemplary embodiment of a cryoablation device in an inflated configuration.

The treatment element 16 may be located at a distal end 52 of the device 12. As shown in FIG. 1, for example, the device 12 may include a treatment element 16 having an inner cryoballoon 18 (which may be referred to simply as "inner balloon") and an outer cryoballoon 20 (which may be referred to simply as "outer balloon"). The inner balloon 18 may include a proximal portion 54 and a distal portion 56, and may define an interior chamber or region 58 that contains coolant or fluid dispersed from the inner balloon fluid delivery conduit defined by or located in the shaft 42, and may be in fluid communication with the inner balloon fluid recovery conduit defined by or located in the shaft 42 for the removal of expended coolant or inflation fluid from the interior 58 of the inner balloon 18. In the non-limiting embodiment shown in FIGS. 1 and 3, the proximal portion 54 of the inner balloon 18 may be coupled to the distal portion 60 of the shaft 42. In the embodiment shown in FIG. 3, the proximal portion 54 of the inner balloon 18 may be coupled to the shaft 42 at a location that is a distance from the distal portion 38 of the elongate body 15, whereas in the embodiment shown in FIG. 1, the proximal portion 54 of the inner balloon 18 may be coupled to the shaft 42 at a location that is proximate the distal portion 38 of the elongate body 15. In either configuration, the distal portion 56 of the inner balloon 18 may also be coupled to the distal portion 60 of the shaft 42 (as shown in FIGS. 1 and 3), proximate a distal tip 64 of the device 12.

Figure 5A:
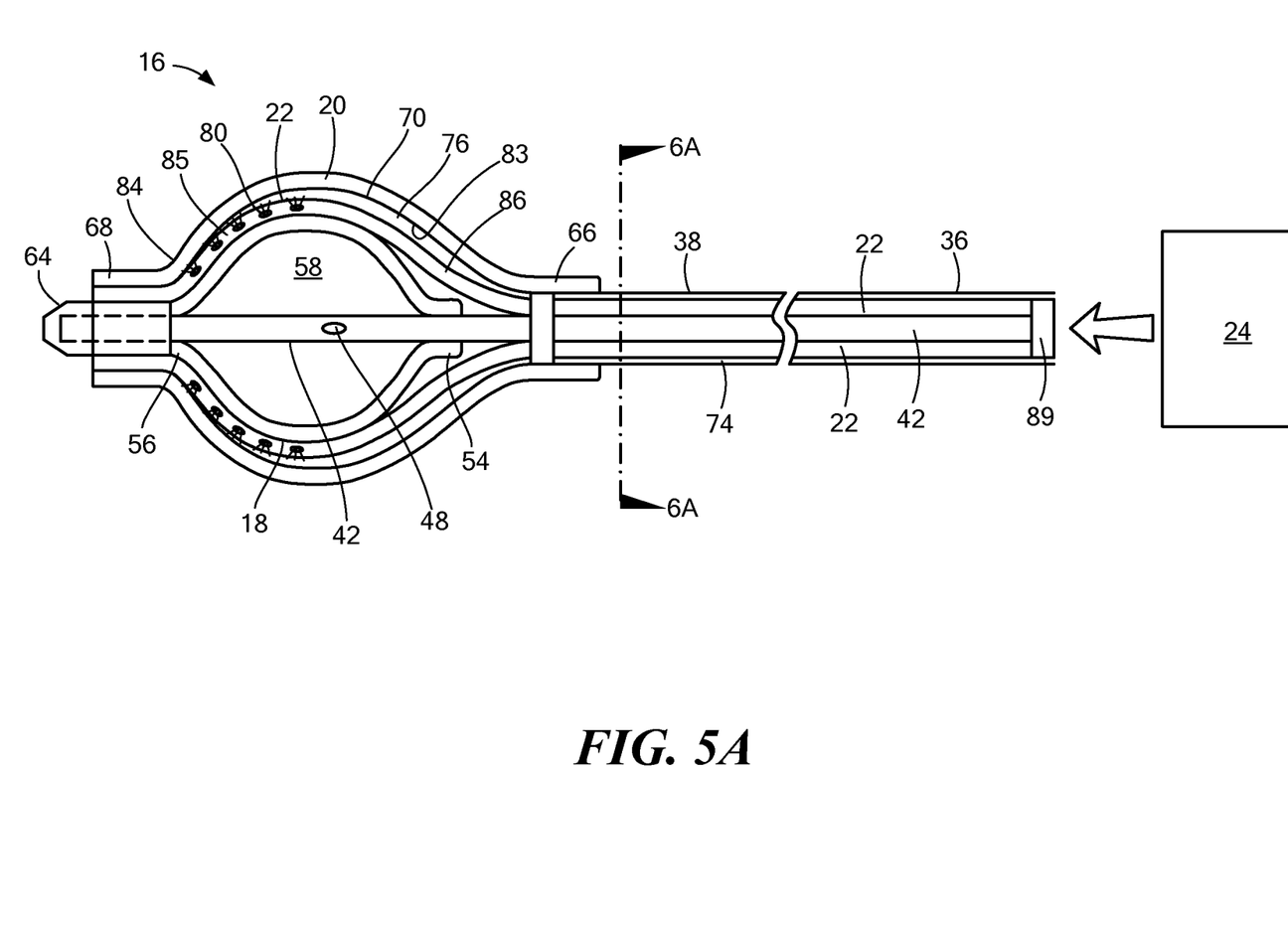
FIGS. 5A and 5B show alternative configurations of coolant ejection ports on a spline.
Figure 5B:
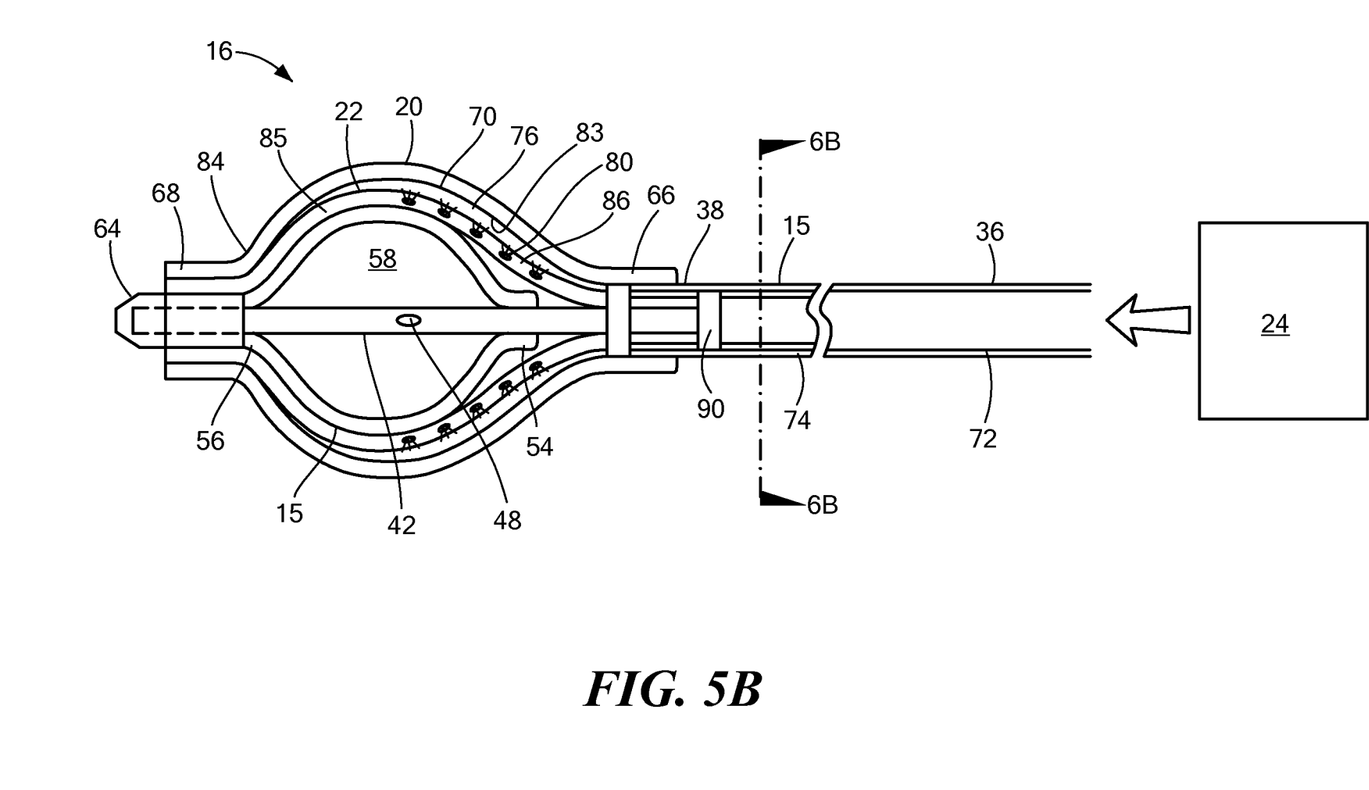
Figure 6A:
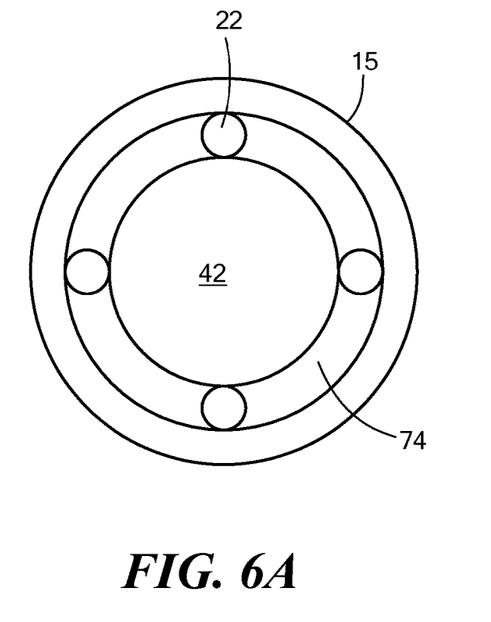
FIG. 6A shows a first cross-sectional view of a fluid delivery conduit in the distal portion of a cryoablation device.
Figure 6B:
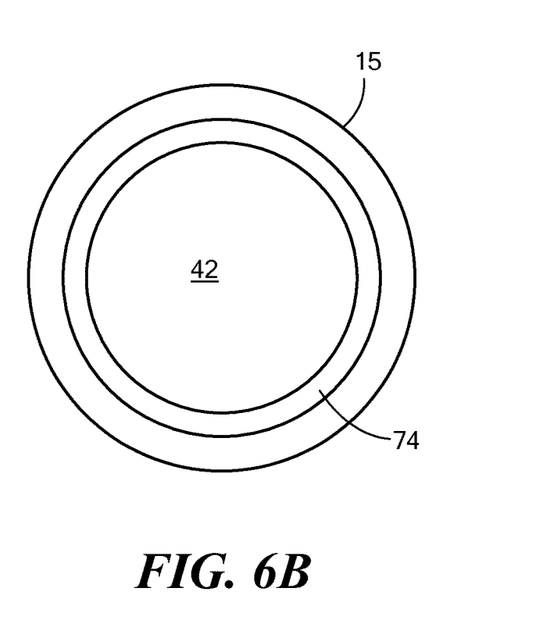
FIG. 6B shows a second cross-sectional view of a fluid delivery conduit in the distal portion of a cryoablation device.

The outer balloon 20 may be disposed about the inner balloon 18. Like the inner balloon 18, the outer balloon 20 may include a proximal portion 66 and a distal portion 68, and may define an interior chamber or region 70 within which the inner balloon 18 is located. The outer cryoballoon 20 may be in fluid communication with an outer balloon coolant delivery conduit 72 defined by or located in the elongate body 15 for delivering coolant from the coolant supply 24 to the outer balloon 20. For example, the outer balloon coolant delivery conduit 72 may be in fluid communication with the one or more splines 22 (as shown in FIGS. 5B and 6B). Alternatively, the one or more splines 22 may extend within the entire, or substantially the entire, length of the elongate body 15, and each spline 22 may be in fluid communication with the coolant supply 24 (as shown in FIGS. 5A and 6A). In that case, the bundle of spline 22 portions disposed within the elongate body 15 may be referred to as the coolant delivery conduit 72. The outer cryoballoon 20 may also be in fluid communication with a fluid recovery conduit 74 defined by or located in the elongate body 15, which may be in fluid communication with the exhaust or scavenging system for the removal of expended coolant or inflation fluid from the interior of the outer balloon 20. The proximal portion 66 of the outer balloon 20 may be coupled to the distal portion 38 of the elongate body 15 and the distal portion 68 of the outer balloon 20 may be coupled to the distal portion 60 of the shaft 42, proximate the distal tip 64 of the device 12.

The proximal 54, 66 and distal portions 56, 68 of both the inner 18 and outer 20 balloons may be coupled to the shaft 42 or elongate body 15 using, for example, a biocompatible adhesive. The outer balloon 20 may further include one or more layers providing for puncture resistance, radiopacity, or the like, and may also be substantially electrically insulative. The inner balloon 18 and outer balloon 20 may be composed of a non-compliant or semi-compliant material (for example, polyethylene terephthalate [PET] or nylon). Alternatively, the outer balloon 20 may be composed of a non-compliant or semi-compliant material whereas the inner balloon 18 may be composed of a compliant material (for example, polyurethane [PU] or nylon elastomers).

The device 12 may further include one or more elongate fluid injection elements, such as splines 22, disposed about the inner balloon 18 and within the outer balloon 20. For example, an interstitial space 76 may be defined between the inner balloon 18 and the outer balloon 20, in which the one or more splines 22 may be located. In the non-limiting example shown in FIG. 5, the device 12 may include four splines 22. Each spline 22 may define a lumen 78 that is in fluid communication with the coolant supply 24, such that the outer balloon 20 is in fluid communication with the coolant supply 24 through the one or more splines 22. Each spline 22 may define a plurality of coolant ejection ports 80. Coolant ejected from the plurality of ports 80 into the interstitial space 76 between the balloons may not only cause the formation of a linear lesion in the tissue with which the treatment element is in contact, but may also cause the outer balloon 20 to inflate (for example, as shown in FIG. 3). Expended coolant within the interstitial space 76 may be recovered through the outer balloon fluid recovery conduit 74 (for example, as shown in FIG. 5A).

Figure 2:
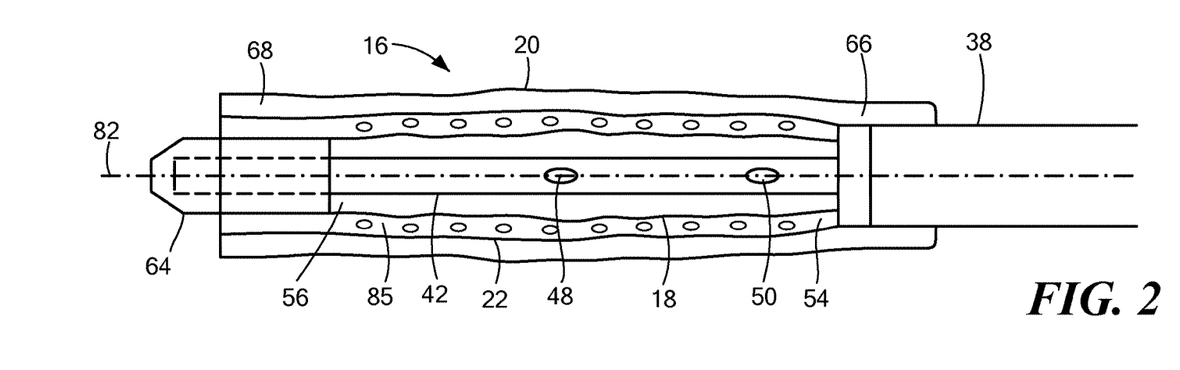
FIG. 2 shows a partial cross-sectional view of a distal portion of a cryoablation device in an uninflated configuration.

The one or more splines 22 may be longitudinally positioned such that when the treatment element 16 is in an uninflated configuration each spline 22 is substantially parallel to the longitudinal axis 82 of the device 12 (as shown in FIG. 2). Further, the one or more splines 22 may be radially arranged about the inner balloon 18 and the longitudinal axis 82 of the device 12. As shown in FIG. 1, for example, the elongate body 15 and the shaft 42 may share the same longitudinal axis 82. Further, the one or more splines 22 may be composed of a deformable biocompatible material, giving the spline(s) the ability to conform to the shape of the inner balloon 18 as the inner balloon 18 is inflated and deflated. That is, inflation of the inner balloon 18 may cause the one or more splines 22 and the outer balloon 20 to radially expand.

Figure 4:
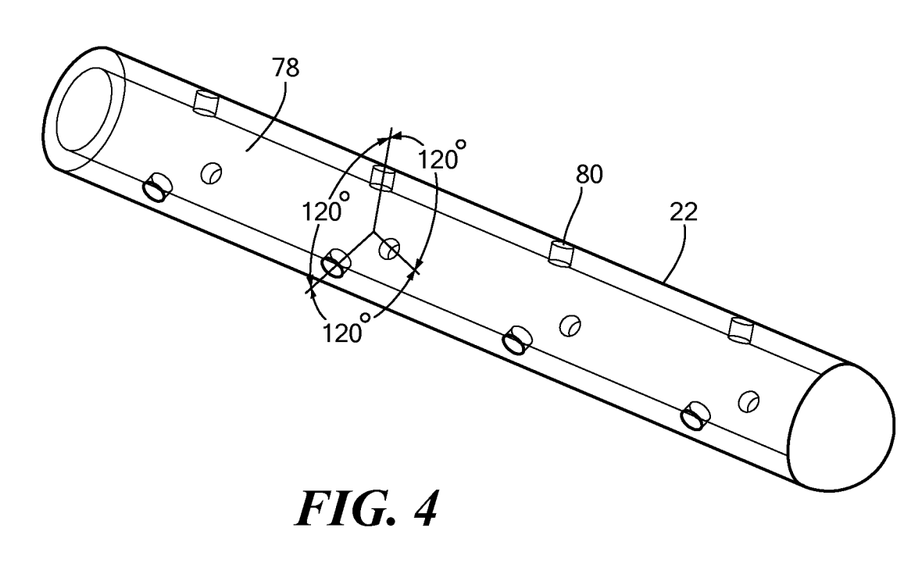
FIG. 4 shows a close-up view of a portion of a spline.

As shown in FIG. 4, the plurality of ports 80 in each spline 22 may be symmetrically positioned about the longitudinal axis 82 of the spline 22. In the non-limiting example shown in FIG. 4, each spline 22 may include a plurality of sets of three ports 80, the three ports 80 being located on the circumference of the spline 22 at approximately 0°/360°, approximately 120°, and approximately 240°. This may create three rows of ports 80 being located on the circumference of the spline 22 at approximately 0°/360°, approximately 120°, and approximately 240°. However, it will be understood that any number and configuration of ports may be used. Further, at least one port on each spline 22 may be oriented toward an inner surface 83 of the outer balloon 20, such that coolant exiting the at least one port 80 impinges on the outer balloon 20 inner surface 83, a configuration that may also be described herein as one or more ports 80 impinging on the inner surface 83 of the outer balloon 20. The pattern of impingement on the inner surface 83 of the outer balloon 20 may cause a reduction in temperature in a corresponding pattern on the outer surface 84 of the outer balloon 20 (referred to as "ablation pattern" on the outer balloon 20). So, if a row of ports 80 impinges on the inner surface 83 of the outer balloon in a linear pattern, a corresponding linear ablation pattern on the outer surface 84 of the outer balloon 20.

Still further, as shown in FIGS. 5A and 5B, and referring to FIG. 3, the ports 80 may be in various locations on each spline 22. In the non-limiting example shown in FIG. 3, the plurality of ports may be located along the entire length of the spline 22 that is disposed within the chamber 58 of the inner balloon 18. Conversely, the plurality of ports 80 may be located on the distal portion 84 (as shown in FIG. 5A) or proximal portion 86 (as shown in FIG. 5B) of the portion of each spline 22 that is disposed within the chamber 58 of the inner balloon 18. The distal portion 84 of each spline 22 may be coupled to the distal portion 60 of the shaft 22 and the proximal portion 86 of each spline 22 may extend into the elongate body 15, where the proximal portion 86 may be coupled to the coolant delivery conduit 72.

The fluid flowpaths (also referred to as "conduits") throughout the device 12 and system 10 (for example, between the control unit 14 and the treatment element 16) may include one or more valves 88 or other devices for regulating the flow of coolant, non-coolant inflation fluid, and/or other fluids through the system 10 and device 12. The one or more valves 88 may be operated either manually or automatically based at least in part on measurements taken by device components such as temperature sensors, pressure sensors, timers, mapping elements, and the like (not shown). Further, each fluid flowpath may be independently regulated, such as by opening and closing one or more valves 88 in the flowpath. For example, one or more valves 88 may be operated as required and/or according to an automatic duty cycle controlled by a processor 34 within a computer 32 of the control unit 14 to regulate inflation of the treatment element, lesion depth and configuration, and temperature of the treatment element and its capacity to remove heat from the target tissue.

Referring now to FIGS. 6A and 6B, cross-sectional views of fluid delivery conduits in the distal portion 52 of a cryoablation device 12 are shown. The cross-sectional view of FIG. 6A is taken along line 6A-6A shown in FIG. 5A, whereas the cross-sectional view of FIG. 6B is taken along line 6B-6B of FIG. 5B. As shown in FIGS. 5A and 6A, each spline may pass through the entirety or substantially the entirety of the elongate body 15. Each spline 22 may be in fluid communication with the coolant supply 24, either individually or through a manifold or coupling element 89. In that case, the bundle of spline 22 portions disposed within the elongate body 15 may be referred to as the outer balloon coolant delivery conduit 72. Although the shaft 42 cross section is shown in FIG. 6A as being solid for simplicity, the shaft 42 may include one or more lumens therethrough, such as a guide wire lumen.

As shown in FIGS. 5B and 6B, the splines 22 may be in fluid communication with the outer balloon fluid delivery conduit 72, for example, within the distal portion 38 of the elongate body 15. The one or more splines 22 may be joined to the outer balloon fluid delivery conduit 72 at a coupling element 90. The coupling element 90 may be disk shaped and may include one or more openings, each sized to allow a spline 22 to pass therethrough. Each spline 22 may terminate inside the delivery conduit 72, either proximate the coupling element 90 or at a distance from the coupling element 90. Fluid may pass from the fluid delivery conduit 72 into the lumen 78 of each spline 22. Further, each opening in the coupling element 90 may have a diameter that is slightly wider than the outer diameter of each spline 22, such that fluid does not escape from the fluid delivery conduit 72 as it passes into the splines 22. Although the shaft 42 cross section is shown in FIG. 6A as being solid for simplicity, the shaft 42 may include one or more lumens therethrough, such as a guide wire lumen.

Figure 7:
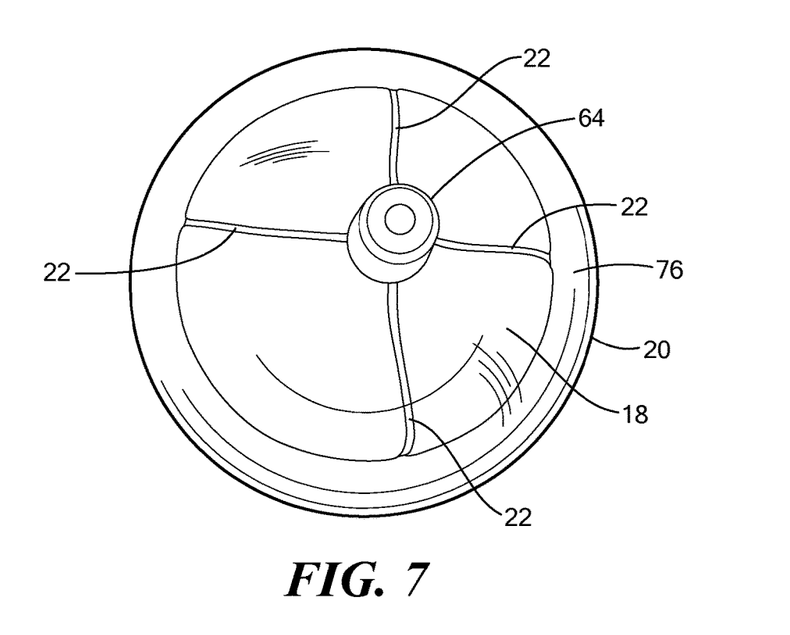
FIG. 7 shows a front view of a cryoablation device treatment element.

Referring now to FIG. 7, a front view of a distal portion 52 of a cryoablation device 12 is shown. The treatment element 16 may include four splines 22 radially arranged about an inner balloon 18 and disposed between the inner balloon 18 and the outer balloon 20. Although four splines 22 are shown in FIG. 7, it will be understood that any number of splines 22 may be used. As a non-limiting example, one, two, three, five, or six splines 22 may be used. Further, when the inflated treatment element 16 is viewed from the front, as shown in FIG. 7, each spline 22 may extend radially from the shaft 42 at approximately a 90° angle. However, each spline 22 may extend radially from the shaft 42 at an angle that is more or less than 90°. As a non-limiting example, each spline 22 may extend at an angle that is between approximately 45° and approximately 135°. The inner balloon 18 may be inflated by the ejection of coolant or non-coolant inflation fluid delivered by the inner balloon fluid delivery conduit, and the outer balloon 20 may be inflated by the ejection of coolant from the plurality of coolant ejection ports 80 defined by the one or more splines 22. The outer diameter Do of the outer balloon 20 may depend, at least in part, on the material from which the outer balloon 20 is composed. For example, a non-compliant balloon may have a maximum outer diameter when fluid is ejected from the one or more splines 22 that is less than the maximum outer diameter of a highly compliant balloon.

Figure 8:
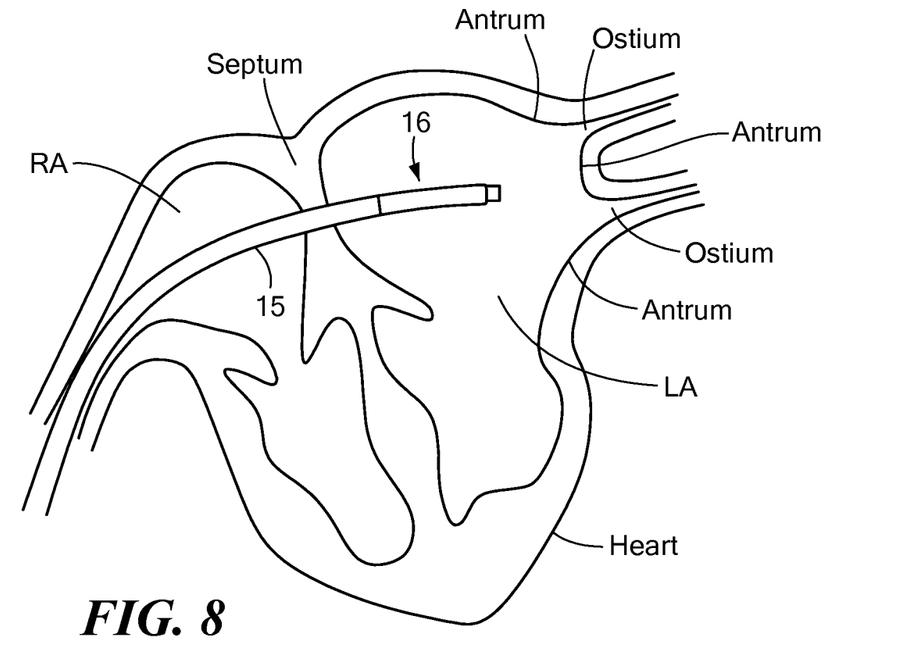
FIG. 8 shows a cryoablation device in an uninflated configuration within the left atrium.
Figure 9:
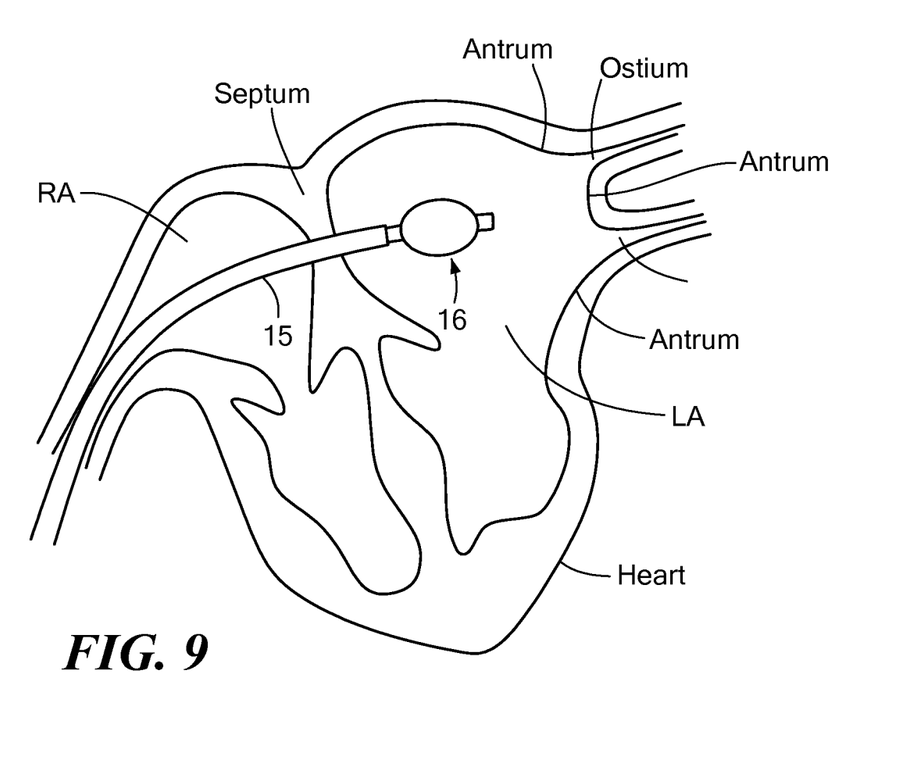
FIG. 9 shows the cryoablation device of FIG. 5 in an inflated configuration within the left atrium.
Figure 10:
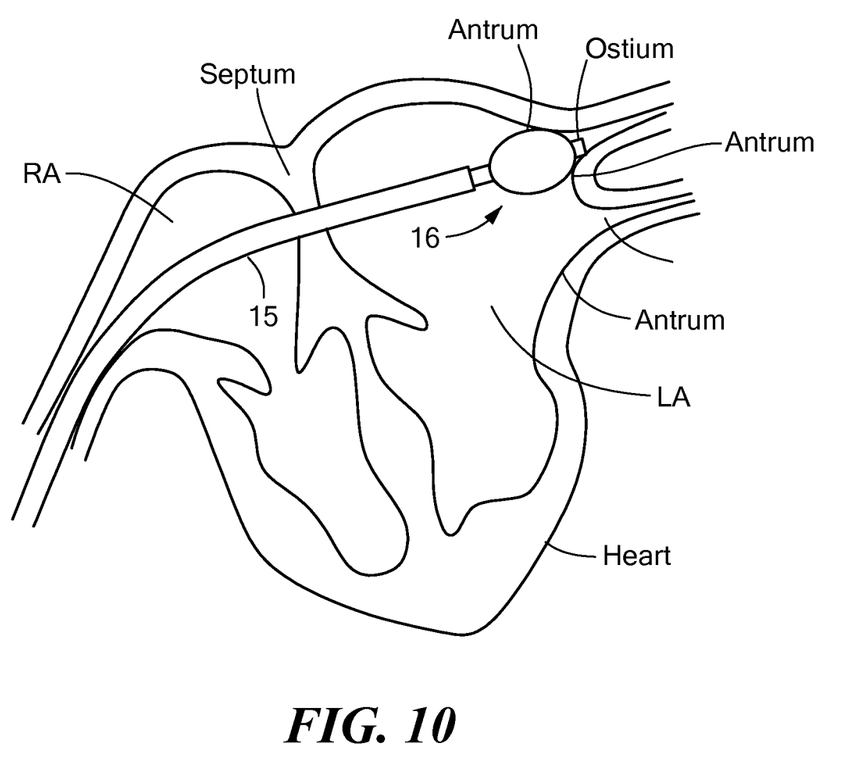
FIG. 10 shows the cryoablation device of FIGS. 5 and 6 in contact with a pulmonary vein ostium and the treatment element activated.

Referring now to FIGS. 8-10, a sequence of events in a cryoablation procedure is shown. In FIG. 8, the device 12 has been delivered to the left atrium (LA) of the patient's heart. For example, a sheath (not shown) may be passed through the patient's vasculature into the right atrium (RA) of the heart, such as by using femoral, brachial, or radial access. Once within the RA, a separate device (not shown) may be passed through the sheath and used to puncture the septum between the RA and LA. The puncture device may then be removed from the sheath and the patient's body, and the device 12 described herein may be passed through the sheath and into the LA. However, it will be understood that other methods of obtaining access to the LA may be used. As shown in FIG. 8, the device 12 may be passed through the patient's vasculature and into the LA with the treatment element 16 in an uninflated configuration.

As shown in FIG. 9, the inner balloon 18 of the treatment element 16 may be inflated once the device 12 is within the LA. For example, the flow of coolant or non-coolant fluid from the coolant supply 24 or the non-coolant supply 30 of the control unit 14 may be initiated. The ejection of this fluid into the chamber 58 of the inner balloon 18 may inflate the inner balloon 18 and, therefore, may likewise expand the outer balloon 20 and the one or more splines 22. As the inner balloon 18 inflates, the one or more deformable splines 22 may bend to conform to the increasing curvature of the inner balloon 18. As shown in FIG. 3, for example, inflation of the inner balloon 18 may cause the one or more splines 22 to transition from a linear configuration that is substantially parallel to the longitudinal axis of the device 12 to an arcuate, radially expanded configuration in which each spline 22 bows outward from the longitudinal axis of the device (for example, the one or more splines 22 may bow outward with respect to the shaft 42). The inner balloon 18 may be inflated before the flow of coolant from the one or more splines 22 between the inner 18 and outer 20 balloons is initiated from the coolant supply 24 of the control unit 14.

As shown in FIG. 10, the device 12 may be positioned in the LA such that at least a portion of the treatment element 16 is placed in contact with the target tissue. The target tissue may include a pulmonary vein ostium, antrum, and/or heart wall. For example, at least a portion of the length at least one spline 22 may be placed in contact with an area of target tissue through the outer balloon 20. If the device 12 includes more than one spline 22, one or more valves and/or other fluid control components may be used to selectively deliver coolant to fewer than all of the splines 22. The size, length, depth, and pattern of lesion(s) 110 created in the target tissue may depend on, for example, the number of splines in the treatment element, the number and location of the splines to which coolant is selectively delivered, and/or the number and location of the fluid ejection ports. It will be understood that the treatment element may cause the formation of linear lesions on the target tissue even when the inner balloon 18 is inflated and the one or more splines 22 have been transitioned to an arcuate configuration (for example, as shown in FIG. 3). This may be because the anatomy of the target tissue is also curved to be in contact with at least a portion of one or more splines, because the inflated treatment element may be slightly compressed by its contact with the target tissue to conform to the shape of the target tissue, and/or because a user may position the treatment element such that at least a portion of at least one spline is in contact with the target tissue.

Figure 11A:
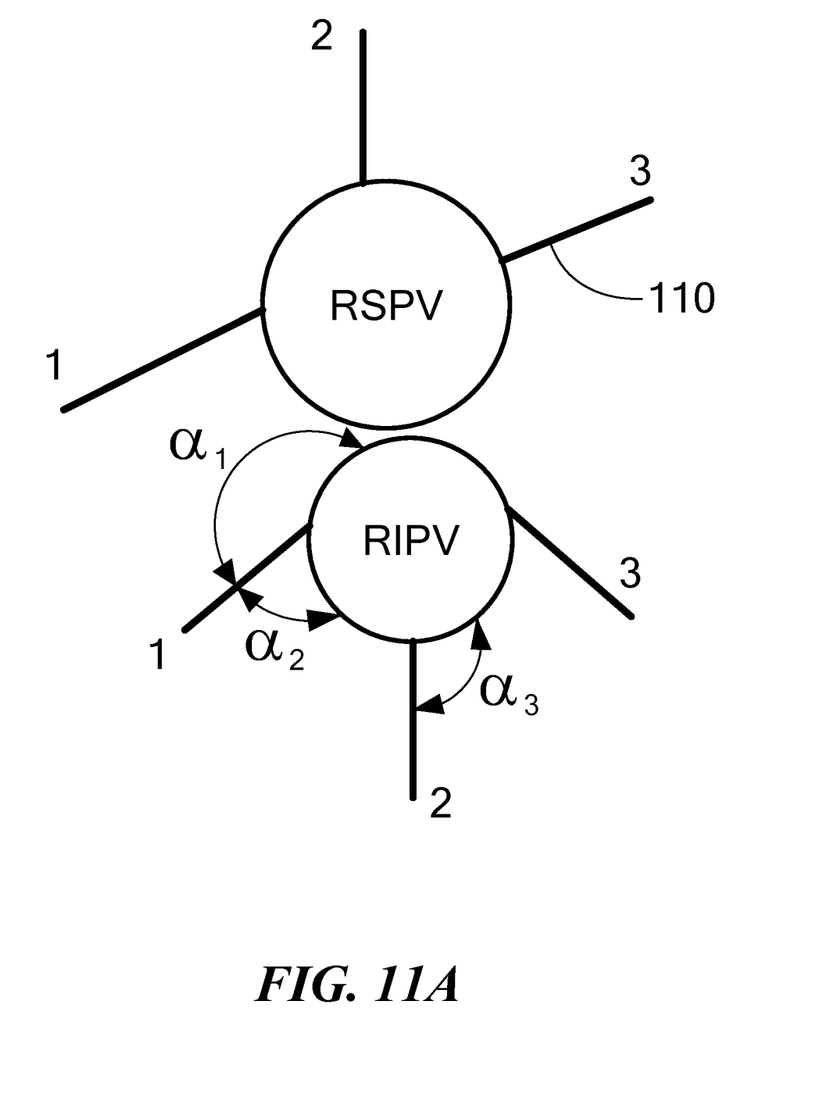
FIGS. 11A and 11B shows an exemplary configuration of radial-linear lesions about the left superior pulmonary vein (LSPV), left inferior pulmonary vein (LIPV), right superior pulmonary vein (RSPV), and right inferior pulmonary vein (RIPV).
Figure 11B:
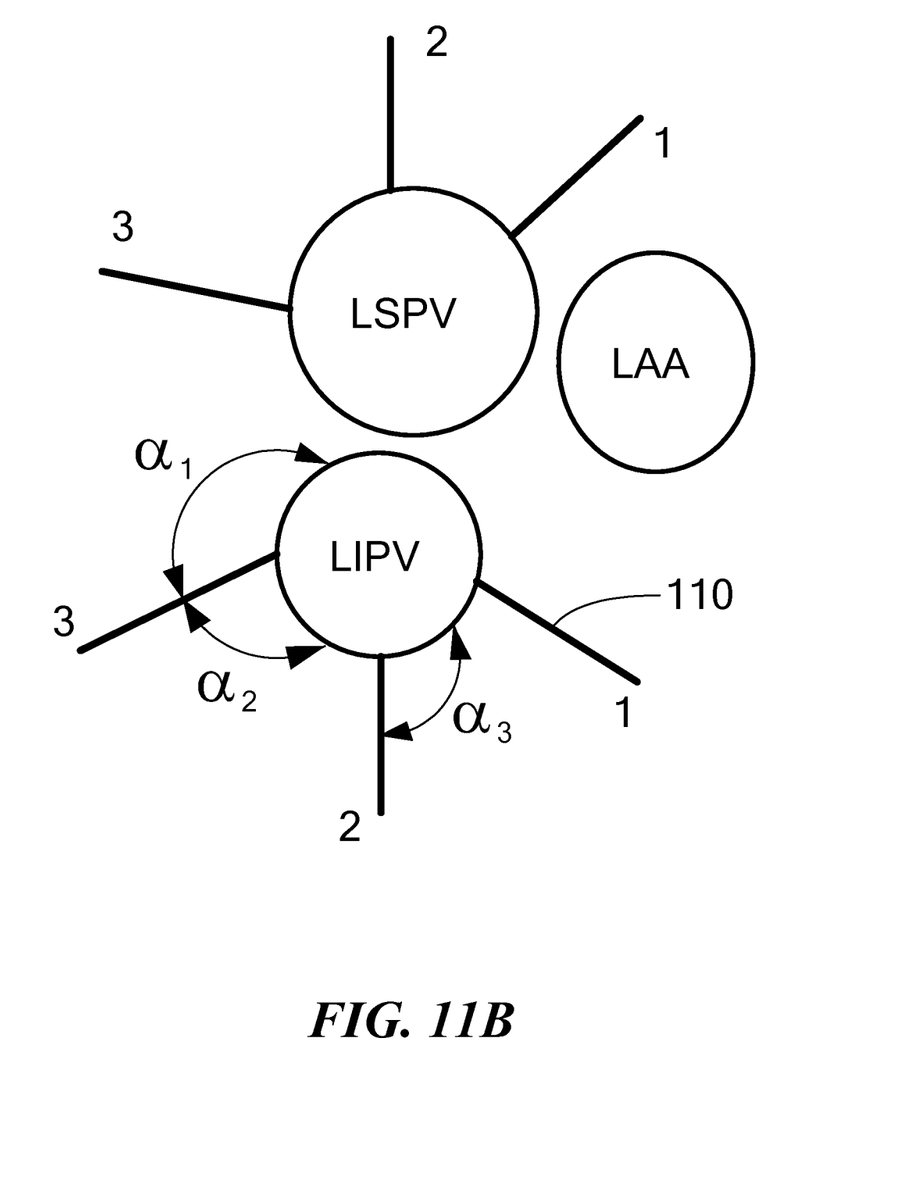

Referring now to FIGS. 11A and 11B, non-limiting examples of radial-linear lesions 110 are shown. Before beginning a PAR ablation procedure, the morphology of the pulmonary veins may be determined using an imaging technique, such as computed tomography angiography. Additionally, tissue within each pulmonary vein, tissue of the antrum, and/or tissue in other areas within the LA may be mapped before the procedure to determine optimal lesion locations. Optionally, imaging technique (for example, venography or computed tomography angiography) may be used during the procedure. The desired pattern of lesions 110 may be determined based on imaging and mapping conducted before the procedure. A cryoablation device having a suitable number and configuration of splines 22 may be selected. Alternatively, a single device may be used for all procedures, with the ejection of coolant from the splines 22 being controlled to create the desired pattern of lesions. For example, to create a pattern of lesions about the RSPV as shown in FIG. 11A, coolant may be selectively ejected from three of, for example, four splines 22. Although it may be possible to create all desired linear lesions simultaneously, the treatment element may also be rotated with respect created lesions to position the splines 22 for the creation of additional linear lesions. For example, if a device 12 includes four splines 22 separated from each other by approximately 90° but mapping and/or imaging indicates that it would be beneficial to create two linear lesions that are close together, the treatment element may be activated to create a first linear lesion or a first set of linear lesions, then rotated by the appropriate degree to position the splines 22 to create a second linear lesion or a second set of linear lesions. As shown in FIGS. 11A and 11B, an optimal ablation pattern may include lesion lines that radially extend from a pulmonary vein at an angle that is more (for example, $\alpha_1$) or less (for example, $\alpha_2$) than 90° (for example, $\alpha_3$).

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device comprising:
   a first balloon;
   a second balloon disposed about the first balloon; and
   one or more splines disposed between the first balloon and second balloon, each spline defining three fluid delivery ports at each of a plurality of locations, the three fluid delivery ports at each of the plurality of locations being radially separated from each other by 120°.

2. The medical device of claim 1, wherein the one or more splines are in fluid communication with a first fluid supply.

3. The medical device of claim 2, wherein the first balloon is in fluid communication with at least one of the first fluid supply and a second fluid supply, the first balloon being transitionable between an uninflated configuration and an inflated configuration.

4. The medical device of claim 3, wherein the first balloon is in fluid communication with the first fluid supply and the second fluid supply, the first fluid supply including a coolant and the second fluid supply including a coolant.

5. The medical device of claim 3, wherein the first balloon is in fluid communication with the first fluid supply and the second fluid supply, the first fluid supply including a coolant and the second fluid supply including a non-coolant inflation fluid.

6. The medical device of claim 3, wherein the one or more splines have a substantially linear configuration when the first balloon is in the uninflated configuration.

7. The medical device of claim 6, further comprising an elongate body and an elongate shaft disposed within and extending distally from the elongate body, wherein the shaft defines a longitudinal axis, the one or more splines being substantially parallel to the longitudinal axis of the shaft when the first balloon is in the uninflated configuration.

8. The medical device of claim 7, wherein each of the one or more splines are radially oriented about the elongate shaft and transitionable between the substantially linear configuration and an arcuate configuration.

9. The medical device of claim 8, wherein each spline has a distal portion and a proximal portion, both the distal portion and proximal portion being located within the second balloon.

10. The medical device of claim 9, wherein the three fluid delivery ports at each of the plurality of locations are located on the distal portion of each spline.

11. The medical device of claim 9, wherein the three fluid delivery ports at each of the plurality of locations are located on the proximal portion of each spline.

12. A medical system comprising:
a cryoablation device defining a longitudinal axis and including:
an elongate body having a distal portion and a proximal portion;
an elongate shaft disposed within the elongate body, the elongate shaft having a distal portion and a proximal portion;
a first balloon coupled to the distal portion of the elongate shaft, the first balloon having an inner surface and an outer surface;
a second balloon disposed about the first balloon and being coupled to the distal portion of the elongate shaft and the and the distal portion of the elongate body, the second balloon having an inner surface and an outer surface; and
one or more splines disposed between the first balloon and second balloon, each spline defining a length within the treatment element, the length having a distal portion and a proximal portion, a circumference, and three fluid delivery ports symmetrically radially spaced around an entirety of the circumference at each of a plurality of locations along the distal portion of the length, at least one of the three fluid delivery ports at each of the plurality of locations along the length being configured to direct a fluid such that the fluid impinges directly against the inner surface of the second balloon; and
a control unit being in communication with the cryoablation device and including:
a first fluid supply in fluid communication with the one or more splines.

13. The system of claim 12, further comprising a second fluid supply in communication with the first balloon.

14. The system of claim 13, wherein the first fluid supply is a coolant and the second fluid supply is a coolant.

15. The system of claim 14, wherein the first fluid supply is a coolant and the second fluid supply is a non-coolant inflation fluid.

16. The system of claim 12, wherein the first fluid supply is also in fluid communication with the first balloon.

17. The system of claim 12, wherein the first and second balloons define an interstitial space therebetween, fluid traveling from the first fluid supply exiting the fluid delivery ports into the interstitial space.

18. A method for creating radial-linear lesions, the method comprising:
positioning a cryoablation device in contact with pulmonary vein antrum tissue of a patient's heart, the cryoablation device including:
an elongate body having a distal portion;
an elongate shaft disposed within the elongate body;
one or more conduits within the elongate body and the elongate shaft; and
a treatment element having:
an inner balloon coupled to the elongate shaft and being in fluid communication with the one or more fluid conduits within the elongate shaft;
an outer balloon disposed about the inner balloon and being coupled to the elongate shaft and the elongate body and being in fluid communication with the one or more fluid conduits within the elongate body; and
one or more longitudinal splines radially disposed between the inner balloon and the outer balloon, each spline defining a circumference and a length extending within the treatment element, the length having a distal portion and a proximal portion, and three fluid delivery ports symmetrically radially spaced around an entirety of the circumference of the spline at each of a plurality of locations along the distal portion of the length, the one or more splines being in fluid communication with a coolant source; and
opening the one or more fluid conduits within the elongate body to the coolant source, coolant from the coolant source passing into the one or more splines and being ejected from the three fluid delivery ports at each of the plurality of locations into an interstitial space defined between the inner balloon and the outer balloon.

19. The method of claim 18, wherein the inner balloon is in fluid communication with a fluid source, the method further comprising:
positioning the cryoablation device within a left atrium of the patient's heart; and
opening the one or more fluid conduits within the elongate shaft to the fluid source, fluid from the fluid source passing into and inflating the inner balloon.

20. The method of claim 18, wherein the one or more splines and the outer balloon are radially expand about the inner balloon when the inner balloon is inflated.

* * * * *

UNITED STATES PATENT AND TRADEMARK OFFICE
CERTIFICATE OF CORRECTION

PATENT NO.        : 10,441,338 B2
APPLICATION NO.   : 14/154747
DATED             : October 15, 2019
INVENTOR(S)       : George D. Mallin and Claudia Lueckge Page 1 of 1

It is certified that error appears in the above-identified patent and that said Letters Patent is hereby corrected as shown below:

In the Claims

Column 11, Line 49, Claim 12 replace "and the and the", with --and the--

Signed and Sealed this
Thirty-first Day of December, 2019

Andrei Iancu
*Director of the United States Patent and Trademark Office*